United States Patent [19]

Kreamer

[11] Patent Number: 5,078,726
[45] Date of Patent: * Jan. 7, 1992

[54] GRAFT STENT AND METHOD OF REPAIRING BLOOD VESSELS

[76] Inventor: Jeffry W. Kreamer, 154 Woodstone Dr., Buffalo Grove, Ill. 60089

[ * ] Notice: The portion of the term of this patent subsequent to Apr. 26, 2005 has been disclaimed.

[21] Appl. No.: 506,853

[22] Filed: Apr. 9, 1990

Related U.S. Application Data

[63] Continuation of Ser. No. 305,807, Feb. 1, 1990, abandoned.

[51] Int. Cl.$^5$ .......................... A61B 17/00; A61F 2/06
[52] U.S. Cl. ........................................ 606/194; 623/1; 623/12
[58] Field of Search ...................... 623/1, 12; 606/191, 606/192, 194, 108

[56] References Cited

U.S. PATENT DOCUMENTS

| | | | |
|---|---|---|---|
| 3,657,744 | 4/1972 | Ersek | 623/11 |
| 3,826,257 | 7/1974 | Buselmeir | 604/8 |
| 3,991,767 | 11/1976 | Miller, Jr. et al. | 604/8 |
| 4,577,631 | 3/1986 | Kreamer | 606/108 |
| 4,740,207 | 4/1988 | Kreamer | 623/1 |
| 4,776,337 | 10/1989 | Palmaz | 606/108 |

Primary Examiner—Stephen C. Pellegrino
Assistant Examiner—Gary Jackson
Attorney, Agent, or Firm—Kent A. Herink

[57] ABSTRACT

A method and apparatus for repairing a weakened section of a vessel. A pair of expandable stents are placed at either end inside a prosthetic graft of a length sufficient to span the weakened section. The graft and stents are inserted into the vessel. The stents are positioned on either side of the weakened section and expanded to a stable, increased diameter for securing by friction the graft in situ inside the vessel.

12 Claims, 2 Drawing Sheets

GRAFT STENT AND METHOD OF REPAIRING BLOOD VESSELS

This application is a continuation of application Ser. No. 07/305,807, filed Feb. 1, 1990, now abandoned.

BACKGROUND OF THE INVENTION

This invention relates generally to stents for holding in situ vascular grafts and, more specifically, to such stents and a method using such stents for repairing diseased or damaged sections of a vessel.

A common health problem is diseased or damaged blood vessels which may weaken, develop into an aneurysm, and rupture. Conventional techniques for the repair of damaged or diseased sections of vessels include invasive surgery to expose to a surgeon the section of the artery to be repaired The weakened section is resected and replaced either by a section of healthy vessel removed from a remote site of the patient s vascular system or by a tubular synthetic graft. Either graft is sutured into place. This prior art technique is traumatic to the patient, frequently requires major surgery, and may be hazardous or impossible to perform if, as is not infrequent, the health of the patient is poor.

A large number of patient admissions and procedures performed each year are due to aneurysms of the aorta that are distal of the renal arteries, i.e., infra-renal abdominal aortic aneurysms. In addition to the resection and replacement procedure, aortic aneurysms are currently repaired by the axillobifemoral bypass method, which method also requires major, invasive, and risky surgery. Recently, a promising new apparatus and procedure for the repair of aortic aneurysms was described in U.S. Pat. No 4,577,631. This procedure is accomplished via a small incision in a femoral artery of the patient and relies on an occlusion catheter to block the arterial flow of blood through the aneurysm site during adhesion of a tubular synthetic graft over the diseased or damaged section of the aorta.

SUMMARY OF THE INVENTION

The present invention is a stent for holding a tubular synthetic graft in place to replace and repair a damaged or diseased section of a vessel. The stent is formed of a generally rectangular section of semi-rigid material The rectangular section is rolled so that an inside longitudinal edge is overlapped by the opposite longitudinal edge. In its relaxed state, the stent is generally cylindrical, having a relatively small diameter and a cross section that is a section of a spiral. The stent can be expanded from its smaller diameter to a larger diameter by partially unrolling the stent, with the result that the cross section is now a shorter section of a spiral having a larger inner and outer diameter. The inner surface of the stent includes a retaining means which acts to restrain the expanded graft from returning to its relaxed, smaller diameter condition.

To repair a section of vessel, a tubular synthetic graft is positioned in place inside the vessel overlapping the weakened section to adjoining healthy sections of the vessel. A stent in its relaxed, smaller diameter condition is positioned at one end inside of the graft and expanded to its enlarged, larger diameter condition, a diameter which is somewhat greater than the inner diameter of the vessel The retaining means prevents the stent from returning to the small diameter condition. Friction between the stent, the graft, and the inner wall of the vessel prevents displacement of the stent and graft once expanded. Similarly, a stent is positioned and expanded at the other end inside of the graft. If necessary, a tie or other means can be placed over the vessel in the region of the stents further to prevent displacement thereof.

DETAILED DESCRIPTION OF A PREFERRED EMBODIMENT

Figure 1:
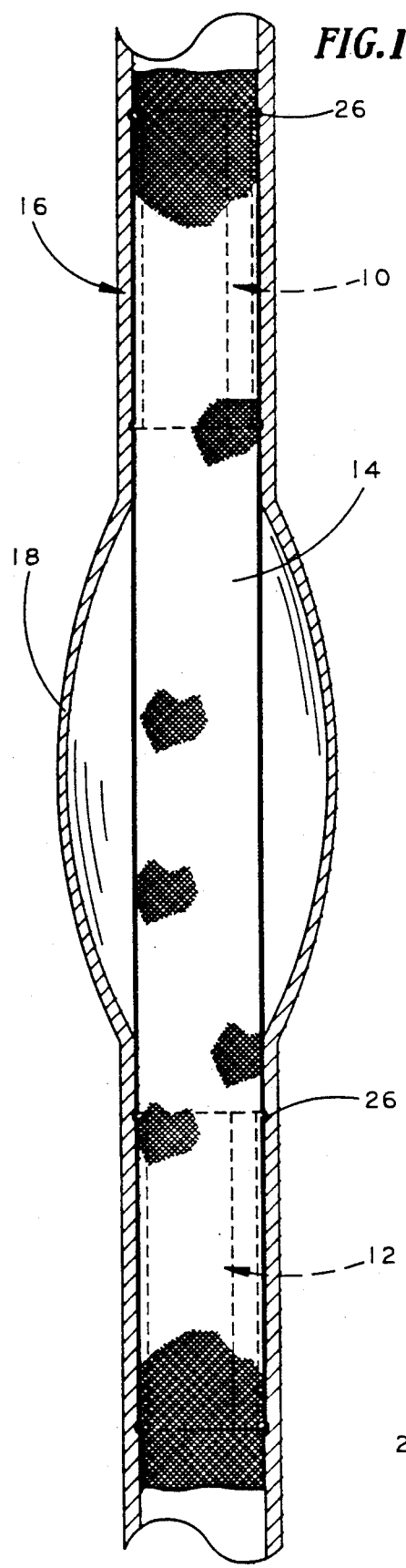
FIG. 1 is a partial, cross-sectional view of a vessel in the region of an aneurysm repaired by the stents and method of the present invention.

Illustrated in FIG. 1 at 10 and 12 are a pair of stents that are used to hold a tubular synthetic graft 14 in place inside a vessel 16 to replace and repair a damaged or diseased section 18 of the vessel. The stents 10 and 12 are identical in construction and may be identical in size. For the purposes of describing the stents 10 and 12, reference will be made to stent 10 only with the understanding that the same description applies to stent 12.

Figure 2:
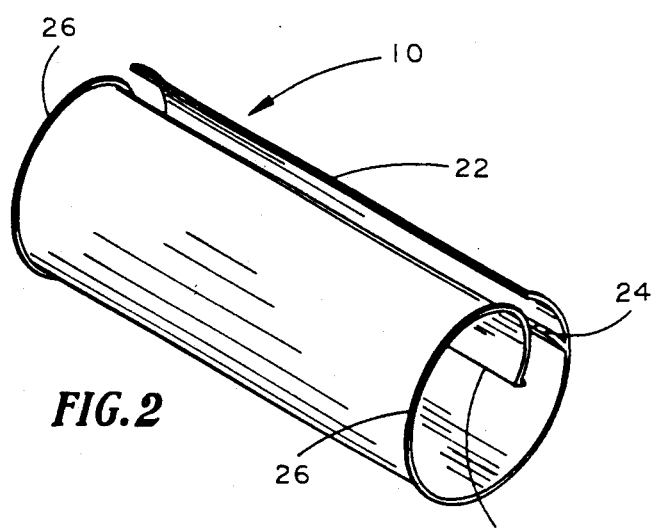
FIG. 2 is a perspective view of a stent in its relaxed, smaller diameter condition.
Figure 3:
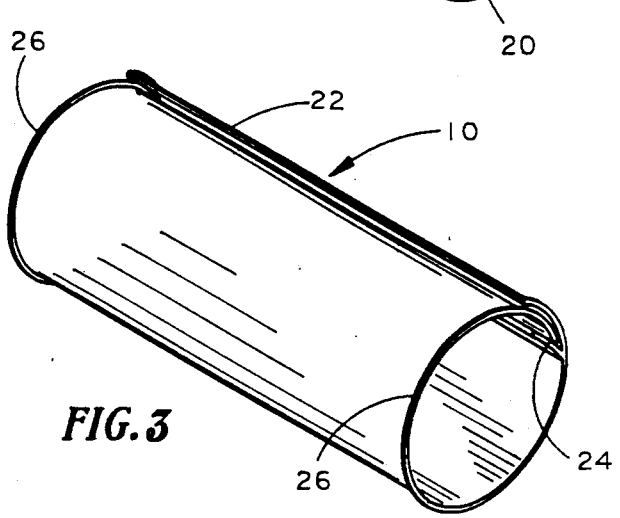
FIG. 3 is a perspective view of a stent in its expanded, enlarged diameter condition.
Figure 4:
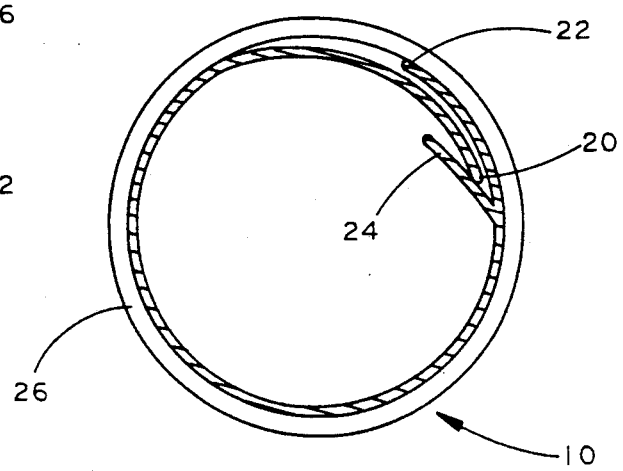
FIG. 4 is a cross-sectional view of the stent expanded inside the vessel.

The stent 10 has a relaxed, smaller diameter condition (FIG. 2 and an expanded, larger diameter condition (FIG. 3). The stent 10 is described fully in U.S. Pat. No. 4,740,207, which patent is incorporated herein by this reference. Briefly, the stent 10 is made of a semi-rigid, generally rectangular piece of material that is rolled so that an inside longitudinal edge 20 is overlapped by the opposite longitudinal edge 22. In its relaxed condition (FIG. 2), the stent 10 requires an expansile force to increase its diameter (FIG. 3). That is, the material comprising the stent 10 is resilient and will attempt to return to its relaxed condition (FIG. 2) unless restrained.

If an expansile force is exerted on the interior of the relaxed stent 10, it will unroll. As it unrolls, the inner longitudinal edge 20 approaches the edge of an inwardly projected restraining tooth 24. A maximum diameter condition is defined wherein the inner longitudinal edge 10 is between the edge of the tooth 24 and the outer longitudinal edge 22. If the expansile force is now released, the resiliency of the stent 10 will cause it to move toward its relaxed condition. The tooth 24, however, captures the inner longitudinal edge 20 and the stent 10 is restrained in its expanded, larger diameter condition (FIG. 3).

Repair of a weakened section of a vessel proceeds by insertion of the tubular synthetic graft 14 into the vessel 16 (FIG. 1). The graft 14 is a conventional tubular graft made of Dacron or Gore-Tex ® (polytetrafluoroethylene) and is of a length sufficient to span the weakened section 18 of the vessel to overlap healthy sections of the vessel 16 on either side of the weakened section 18.

Figure 5:
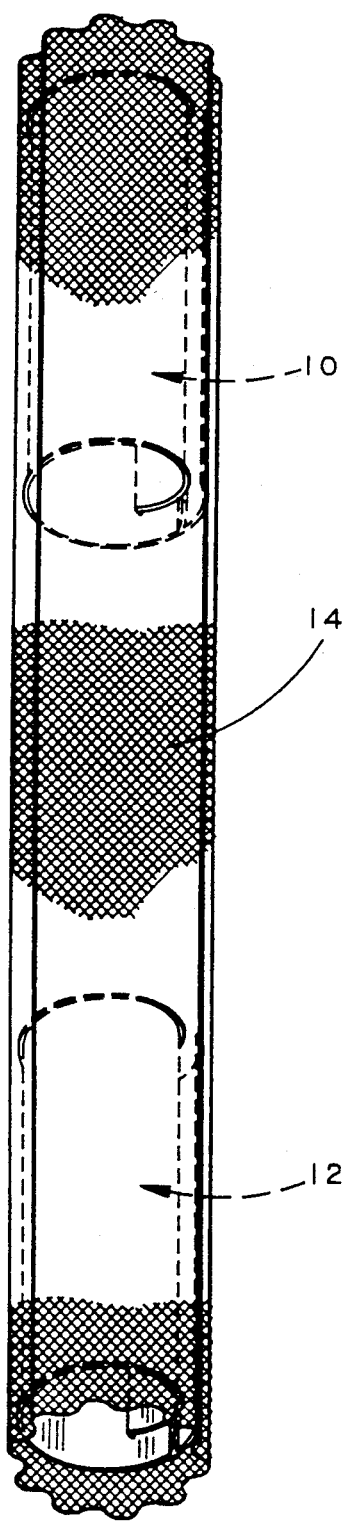
FIG. 5 is a perspective view of two stents in their smaller diameter condition located inside a tubular synthetic graft.
Figure 6:
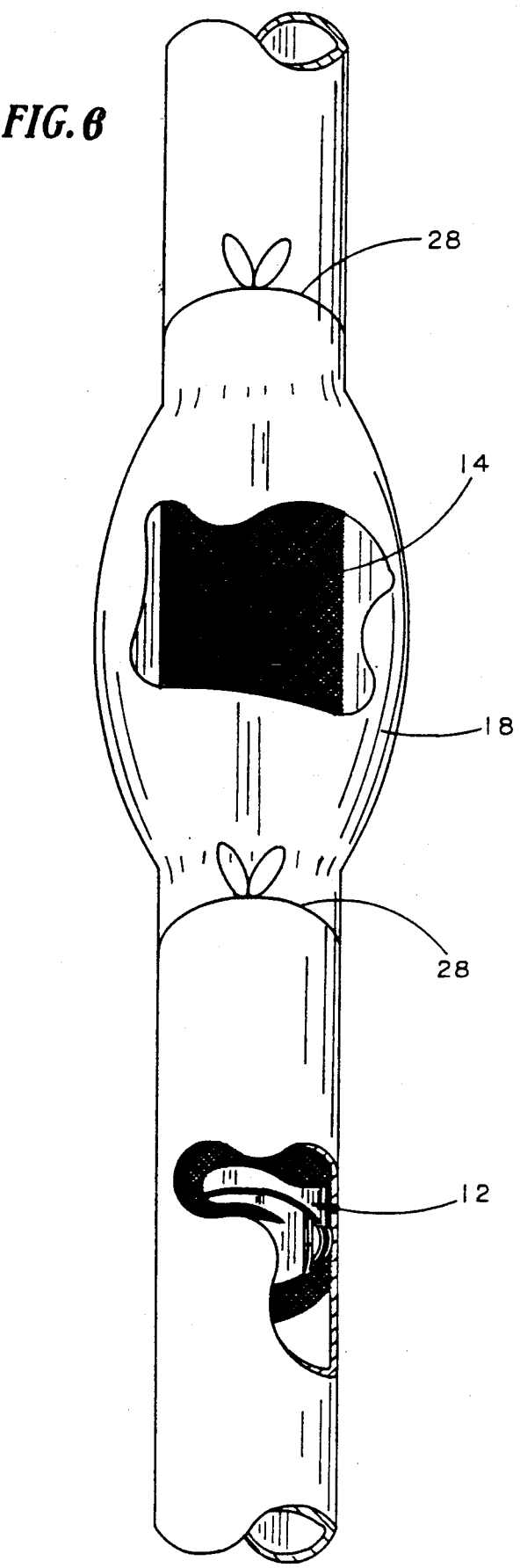
FIG. 6 is a perspective view of a vessel repaired using the stents and method of the present invention with parts broken away to show the graft and stents inside the vessel.

Once the graft 14 has been appropriately positioned in the vessel 16, the stent 10 is its relaxed condition is inserted into the graft 14 (FIG. 5) and the vessel 16 and properly positioned on one side of the weakened section 18. It is then expanded to its maximum diameter and released to its expanded, larger diameter condition (FIG. 1). Similarly, the stent 12 is positioned inside the graft 14 and vessel 16, appropriately positioned, and expanded to its expanded-larger diameter condition. The stents 10 and 12 are chosen to be of an expanded, larger diameter that is larger than the ordinary inside diameter of the vessel 16 in the areas where the stents will be placed. The stents, accordingly, will be expanding somewhat the natural diameter of the vessel 16. The combination of stent, vessel, and intervening graft will be held relatively stationary by the friction between the different elements A raised lip 26 (FIGS. 1-3) is provided at either end of the stents 10 and 12 to further increase the holding ability of the stents. If additional security against movement is desired, a tie 28 (FIG. 6) may be applied outside the vessel 16 in the area of the stents. Alternatively, a clamp or suitable tape could be applied to further secure the stents and graft. Further, the stents could be held captive to the graft, e.g., in sleeves or pockets at either end of the graft.

While the stents 10 and 12 can be used instead of sutures in the conventional resection procedure, a less invasive method of repairing the weakened section is preferred. One such method is a modification of the aneurysm repair method described in U.S. Pat. No. 4,577,631, which patent is incorporated herein by this reference. The stent 10 of the present invention is placed inside the graft of the '631 patent and the balloon catheter thereof is used to expand the stent to hold the graft in place. The stent 10 thus takes the place of the '631 patent of the adhesive for securing the graft to the vessel.

A second less invasive method would make use of a double balloon catheter that is similar to the triple balloon catheter (50) of the '631 patent except that only two balloon sections are required. In this method, a graft of the appropriate length and diameter is selected. Two stents having the appropriate expanded, larger diameter are received about the noninflated balloons of the catheter that have been positioned a distance apart sufficient to span the weakened section of the vessel to be repaired. The graft is then received about the stents and catheter. It may be desirable to secure the graft to the exterior of the stent or stents so that it is not displaced therefrom during the procedure.

An incision is made in the vessel at a site remote from the weakened section. In the case of an infra-renal aortic aneurysm, the incision may be made into a femoral artery in the leg of the patient. The catheter carrying the stents and graft is inserted into the incision and fed to the site of the weakened section. As described in the '631 patent, a radio-opaque equator on the balloons may assist in placement of the catheter. Once the catheter is in position, the balloons are inflated to expand the stents to their maximum diameter and then deflated. As described above, the stents will be restrained in their expanded, larger diameter condition and will hold the graft in place thereby repairing the weakened section of vessel. This method can, of course, be adapted (as can the other methods herein described) to make use of a bifurcated or Y-shaped graft for use, for example, in performing an axillobifemoral bypass.

I claim:

1. An apparatus for repairing a weakened section of a vessel, comprising:
   (a) a tubular graft for lining the interior of the unresected vessel and of a length sufficient to span the weakened section of the vessel;
   (b) a pair of generally cylindrical stents expandable from a relaxed, smaller diameter condition to an enlarged, larger diameter condition;
   (c) wherein said stents are positioned inside end portions of said graft and separated by a distance greater than the length of the weakened section; and
   (d) wherein said stents are expanded from said smaller diameter condition to said larger diameter condition for securing said graft inside the vessel and spanning the weakened section thereof.

2. The apparatus as defined in claim 1, further comprising:
   (a) means applied outside the vessel at the locations of said expanded stents for further securing said stents and graft in position inside the vessel.

3. The apparatus in claim 2, wherein:
   (a) said securing means is a length of suture tied about the vessel.

4. The apparatus as defined in claim 1, wherein said stents are substantially impenetrable by bodily tissues.

5. The apparatus as defined in claim 1, wherein said stents are unfenestrated.

6. The apparatus as defined in claim 1, wherein said stents when in said enlarged, larger diameter have a substantially equal diameter over the length thereof.

7. A method for repairing a weakened section of a vessel, comprising the steps of:
   (a) inserting a graft inside the vessel that is of a length to span the weakened section thereof;
   (b) inserting an expandable stent wholly inside said graft on either side of the weakened section;
   (c) expanding said stents to a stable, expanded condition for securing said graft to the vessel on either side of the weakened section.

8. The method defined in claim 7, wherein
   (a) said graft and inserted stents are received about a double balloon catheter whereby each of said stents is located at a balloon of the catheter;
   (b) making an incision in the vessel at a site remote from and communicating with the weakened section;
   (c) feeding into the vessel said balloon catheter; and
   (d) enlarging said balloon catheter to expand each of said stents to a stable, expanded condition for securing said graft to the vessel on either side of the weakened section.

9. The method as defined in claim 7, further comprising the step of:
   (a) applying to the outside of the vessel at the locations of said expanded stents means for further securing said stents and graft in position inside the vessel.

10. The method as defined in claim 7, wherein the vessel lining grows only over a free end portion of said stents.

11. The method as defined in claim 7, wherein the vessel remains open to the circulation of blood during repair of the vessel.

12. The method as defined in claim 7, wherein said graft resides partially within the weakened section.

* * * * *

UNITED STATES PATENT AND TRADEMARK OFFICE
CERTIFICATE OF CORRECTION

PATENT NO. : 5,078,726
DATED : January 7, 1992
INVENTOR(S) : Kreamer, Jeffry W.

It is certified that error appears in the above-indentified patent and that said Letters Patent is hereby corrected as shown below:

On the title page, item [63] Related U.S. Application Data, change "Feb. 1, 1990" to read --Feb. 1, 1989-- therefor.

Signed and Sealed this

Seventh Day of September, 1993

Attest:

BRUCE LEHMAN

Attesting Officer      Commissioner of Patents and Trademarks